US008059827B2

(12) United States Patent
Klossowski

(10) Patent No.: US 8,059,827 B2
(45) Date of Patent: Nov. 15, 2011

(54) NOISE REDUCTION APPARATUS

(75) Inventor: Uwe Klossowski, New Bern, NC (US)

(73) Assignee: BSH Home Appliances Corporation, Huntington Beach, CA (US)

( * ) Notice: Subject to any disclaimer, the term of this patent is extended or adjusted under 35 U.S.C. 154(b) by 1430 days.

(21) Appl. No.: 11/581,905

(22) Filed: Oct. 16, 2006

(65) Prior Publication Data

US 2008/0089529 A1 Apr. 17, 2008

(51) Int. Cl.

| | |
|---|---|
| ***A61F 11/06*** | (2006.01) |
| ***G10K 11/16*** | (2006.01) |
| ***H03B 29/00*** | (2006.01) |

(52) U.S. Cl. ...................................... 381/71.3; 381/71.7

(58) Field of Classification Search ................. 381/71.3, 381/71.2, 71.1, 71.14, 71.8, 114, 94.3, 94.6

See application file for complete search history.

(56) References Cited

U.S. PATENT DOCUMENTS 4,166,197 A * 8/1979 Moog et al. ................... 381/101
5,129,003 A * 7/1992 Saruta .......................... 381/71.3
5,410,607 A * 4/1995 Mason et al. ................ 381/71.2
6,178,246 B1 1/2001 Bebesel et al.
6,654,467 B1 * 11/2003 York et al. ................. 381/71.14
6,768,799 B1 * 7/2004 Thomas ........................ 381/71.3

FOREIGN PATENT DOCUMENTS

DE 39 16 031 12/1989
DE 39 16 030 11/1990
DE 198 36 483 2/2000

OTHER PUBLICATIONS

National Search Report DE 10 2006 060 032.0.

* cited by examiner

*Primary Examiner* — Xu Mei

(74) *Attorney, Agent, or Firm* — James E. Howard; Andre Pallapies

(57) ABSTRACT

A passive noise reduction apparatus for altering predetermined sound levels of a sound producing device, the noise reduction apparatus includes at least one piezoelectric foil sensor disposed relative to the sound producing device with the at least one piezoelectric foil sensor being operable to convert such sound wave energy into an electric sound signal and one or more electric circuits in electrical communication with the at least one piezoelectric foil sensor for receiving the electric sound signal and shunting the electric sound signal to a ground connection, thereby reducing sound heard outside the sound producing device.

7 Claims, 4 Drawing Sheets

NOISE REDUCTION APPARATUS

BACKGROUND OF THE INVENTION

The present invention is directed broadly to apparatus for altering sound energy in the form of passively reducing noise emitted from appliances for residential and commercial settings and, more particularly, to an apparatus for altering sound energy in a manner that passively reduces such sound energy in the form of noise produced during the operation of residential or home appliances.

In the present case, passive noise reduction refers to noise reduction without input to the appliance at issue. On the other hand, an active noise reduction system provides some sound negating input to the appliance, either electrical or in the form of cancelling sound wave energy.

Large household appliances such as dishwashers, refrigerators, laundry machines, including washers and dryers, and even smaller household appliances such as oven hood vent fans, wine coolers, espresso-making apparatus, food mixers, food processors, juice centrifuges, juice extractors, and waste masticators all emit a certain amount of sound in the form of noise in connection with the operation of fans, electric drive motors, pumps, compressors, or other customary components of such appliances. Such sound emissions may be objectionable as noise to some and to others may just appear as loud sound energy. The use and accommodation of such appliances within residences and other settings would be improved if there existed a capability to selectively alter the sound level including altering the sound level to a reduced (lower decibel) level.

To that end, much time and effort has already been expended in providing insulation for sound producing components of such appliances, in providing more balancing of such sound producing components, and in more efficiently using electricity so as to reduce the emitted noise. The insulation helps to reduce the noise heard outside of the sound producing device and, indeed, much progress has been made in reducing noise from household appliances. On the other hand, it is generally understood that to further lower noise or sound emissions from these appliances would be desirable and will in fact advance the desired goal of full seamless integration of such appliances into the full range of residential and commercial settings. It would therefore be desirable if other methods and apparatus beyond the known insulation, balancing, and energy efficiency approaches were available to help reduce the sound level emitted from such sound producing home appliances.

SUMMARY OF THE INVENTION

To those collective ends, it is accordingly an object of the present invention to provide a noise reduction apparatus for altering predetermined sound levels from a sound-producing device such as a home appliance, wherein the noise reduction apparatus provides efficient sound reduction for a relatively low cost.

In furtherance thereof, and according to one embodiment of the present invention, there is provided a noise reduction apparatus for passively altering sound in the manner of reducing predetermined sound levels of a sound producing device. The noise reduction apparatus includes at least one piezoelectric sensor disposed relative to the sound producing device such that the at least one piezoelectric sensor is influenced by sound wave energy emitted from the sound producing device with the at least one piezoelectric sensor being operable to convert such sound wave energy into an electric sound signal. The present invention further includes an electric circuit in electrical communication with the at least one piezoelectric sensor for receiving the electric sound signal, the electric circuit including a ground connection and being configured for shunting the electric sound signal to the ground connection, thereby reducing sound heard outside the sound producing device.

The at least one piezoelectric sensor may be a foil type or a ceramic type sensor. The electric circuit off the present invention may also include at least one resistor for dissipating at least a portion of the electric sound signal as heat. Further, the present invention may include an array of piezoelectric sensors disposed at spaced intervals relative to the sound producing device. The array may contain all foil sensors, all ceramic sensors or a mixture of the two.

According to one aspect of the present invention, the sound producing device may be a dishwasher having a pump, and the at least one piezoelectric sensor is disposed relative to the pump such that the at least one piezoelectric sensor is influenced by sound wave energy emitted from the pump. In addition the sound producing device may be a dishwasher having a pump and a dishwashing compartment with the array of piezoelectric sensors including at least one sensor disposed within the sound producing device for sensing pump sound and at least one other sensor disposed adjacent the dishwashing compartment for sensing sound produced by water circulating within the dishwashing compartment.

The noise reduction apparatus of the present invention is adaptable to several home appliances. These may include a selected one of a dishwasher, a clothes washer, a clothes dryer, a refrigerator, a ventilation device, a wine cooler, an espresso making apparatus, a food mixing machine, a food processor, a juice centrifuge, a juice extractor and a waste masticator. Here, the at least one piezoelectric sensor is influenced by sound wave energy emitted from the selected sound producing device with the at least one piezoelectric sensor being operable to convert such sound wave energy into the electric sound signal.

The present apparatus can be configured to operate in coordination with different modes of operation of the host appliance. According to another embodiment of the present invention, a noise reduction apparatus for altering predetermined sound levels of a sound producing device, the noise reduction apparatus includes at least one piezoelectric sensor disposed relative to the sound generating device for sensing sound wave energy emitted therefrom and converting the sound wave energy to an electric signal. The present invention further includes a first electric circuit in electrical communication with the at least one piezoelectric sensor for receiving the electric sound signal, the first electric circuit including a ground connection and being configured for shunting the electric sound signal to the ground connection and a second electrical circuit in the form of a control circuit in electrical communication with the first electrical circuit for controlling operation thereof, the control circuit having at least two selectively engagable operational modes including a first mode for real-time monitoring of the second electrical signal for controlling the third electrical circuit responsive thereto, and a second mode for operating the third electrical circuit in conjunction with predetermined operational modes of the sound producing device, thereby reducing sound heard outside the sound producing device.

The apparatus of the present invention may also include an array of piezoelectric sensors disposed at spaced intervals relative to the sound generating device. The piezoelectric sensors may be foil type or ceramic type sensors as needed.

As with the other previously addressed embodiment, the present invention may include a dishwasher having a pump and the at least one piezoelectric sensor is disposed relative to the sound producing device for sensing pump sound. Further, the present invention may include a dishwasher having a pump and a dishwashing compartment with the array of piezoelectric foil sensors including at least one sensor disposed relative to sound producing device for sensing pump sound and at least one sensor disposed relative to the dishwashing compartment for sensing sound produced by water circulating within the dishwashing compartment.

In accordance with prior-discussed embodiments, the sound generating element may be associated with a device selected from the group consisting of a dishwasher, a clothes washer, a clothes dryer, a refrigerator, a ventilation device, a wine cooler, an espresso making apparatus, a food mixing machine, a food processor, a juice centrifuge, a juice extractor and a waste masticator and the at least one piezoelectric sensor is influenced by sound wave energy emitted from the selected sound producing device with the at least one piezoelectric sensor being operable to convert such sound wave energy into the electric sound signal.

The present invention is adaptable in to various appliances in increasing levels of complexity and provides noise reduction capabilities beyond those attainable with known insulation, balancing, and energy efficiency approaches alone.

DESCRIPTION OF THE PREFERRED EMBODIMENTS

Turning now to the drawings and, more particularly to FIG. 1, there is illustrated in a front plan view in partial section, a dishwasher 10, it being noted that this dishwasher 10 is hereinafter described as an exemplarily appliance having sound producing components disposed therein and which is amenable to be configured with an embodiment of the passive noise reduction apparatus of the present invention to favorably alter the noise characteristics of the dishwasher. It should also be noted that the noise reduction methods and apparatus applied with respect to the present dishwasher 10 are equally applicable to other sound producing items including, but not limited to, a clothes washer, a clothes dryer, a refrigerator, a ventilation device such as a range hood, a wine cooler, an espresso making apparatus, a food mixing machine, a food processor, a juice centrifuge, a juice extractor and a waste masticator. All these items have some form of sound producing apparatus or device in common. It should be apparent to those skilled in the art that the sensors, as will be explained in greater detail hereinafter, should be placed strategically in the area of the sound producing element within the device so that they may sense the sound emitted therefrom.

Additionally, it is noted that the present invention is operable to reduce sound energy that may be described as "noise" heard outside the housing or container of one of the aforesaid appliances or any other appliance that may be adaptable to such technology. Herein, when discussing noise, a certain amount of subjectivity is involved in that the term noise generally indicates a harsh or unpleasant sound. The present invention is configured for reducing sound in general and basically is intended to alter the sound emitted from appliances. Accordingly, while such sound alteration may not amount to noise reduction according to some listeners, such sound alteration when referred to as noise reduction should not be considered beyond the scope and spirit of the present invention.

Figure 1:
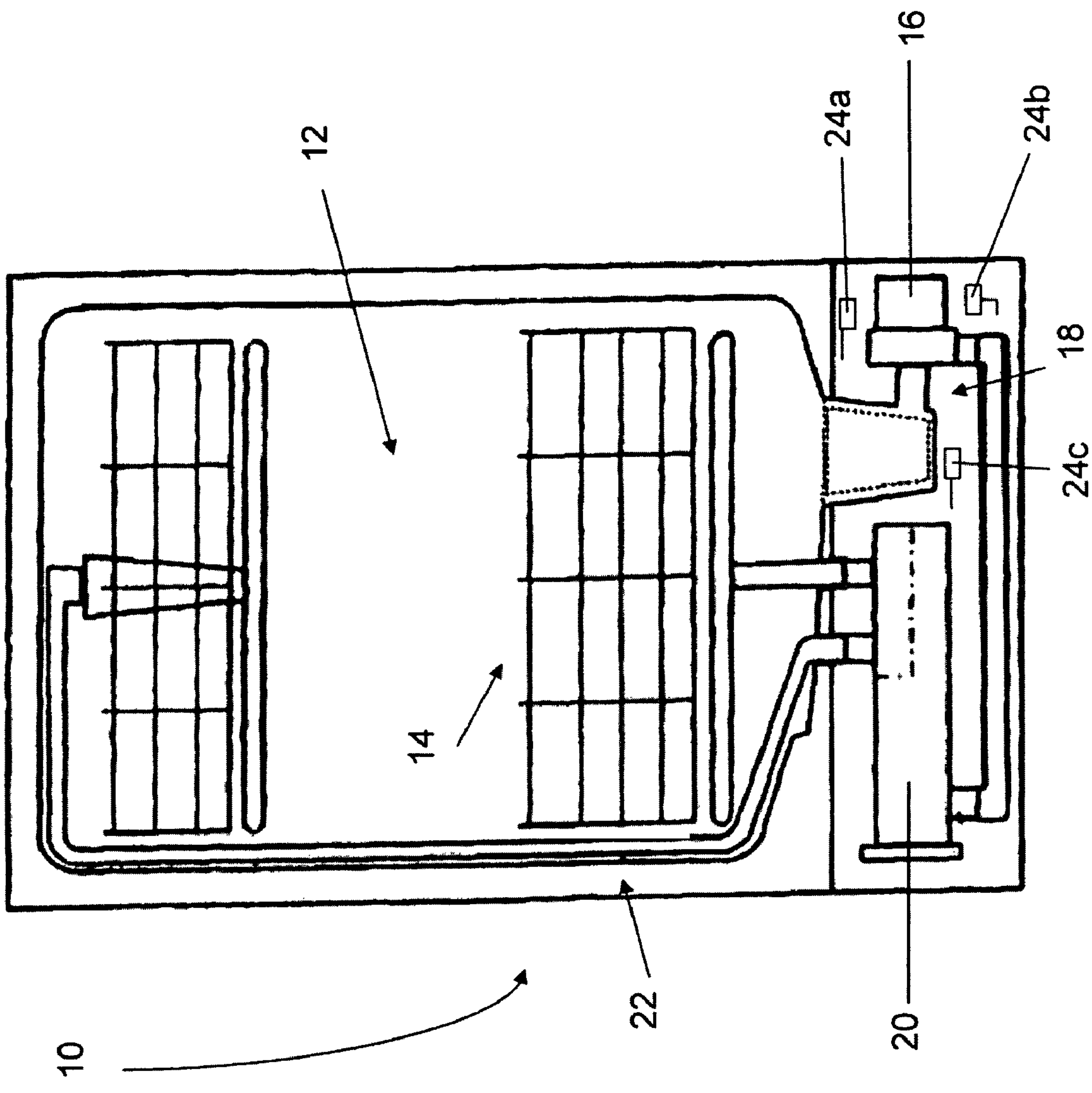
FIG. 1 is a front plan view, in partial section, of a dishwasher configured with one preferred embodiment of the present invention.

With continued reference to FIG. 1, a dishwasher 10 includes a washing compartment 12 containing one or more racks 14 for holding dishes or other household items to be cleaned. Water is driven through the dishwasher 10 by a pump 16 disposed underneath the washing compartment 12 in a pump housing or area 18, which may or may not be isolated structurally from the washing compartment 12. The particular dishwasher 10 illustrated includes a flow heater 20 that receives water from the pump 16 and delivers the heated water into the washing compartment 12 through water lines 22. As may be expected, noise may be generated by the pump 16, the flow heater 20, water flowing through the water lines 22 as well as water bombardment within the washing compartment 12. Even though components such as the pump 16 are chosen and mounted within the dishwasher 10 in a manner designed to reduce noise, noise or sound heard outside of the appliance is not completely eliminated.

According to the one preferred embodiment of the present invention, piezoelectric foil sensors 24*a*, 24*b* and 24*c* are placed within the pump housing 18 in an area adjacent the pump 16 or in an area sufficient that they receive sound wave energy from the pump 16. The piezoelectric foil sensors 24*a*, 24*b* and 24*c* are connected to ground in order to shunt the sound signal to ground. Alternately, the sensors discussed above as piezoelectric foil sensors may be formed as ceramic piezoelectric sensors to provide, among other things, a measure of water resistance in the sensors.

Figure 2:
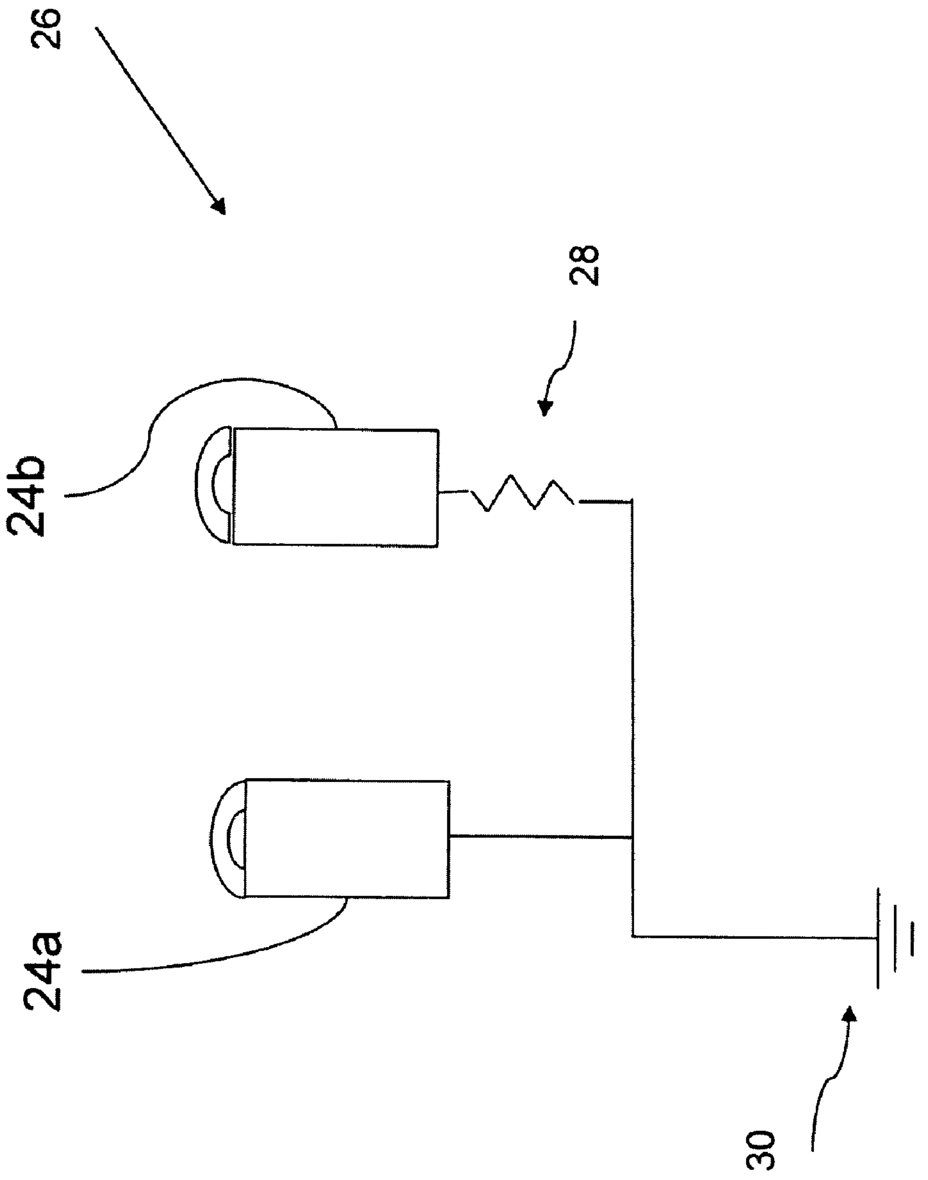
FIG. 2 is a diagrammatic view of an electrical circuit of the present invention according to a further preferred embodiment thereof.

The piezoelectric foil sensors receive sound wave energy and are vibrated thereby. As with any piezo-based device, such vibrations are converted to electrical energy by the piezo device. As seen in FIG. 2 in which a further preferred embodiment of the noise reduction apparatus of the present invention is illustrated, the noise reduction apparatus of the present invention is illustrated at 26 and includes a resistor 28 that may be placed in the circuit intermediate a piezoelectric sensor (here, for illustration purposes the sensor illustrated at 24*b*) and a ground connection 30 to dissipate some of the electrical energy generated by the piezoelectric sensor as heat.

Figure 3:
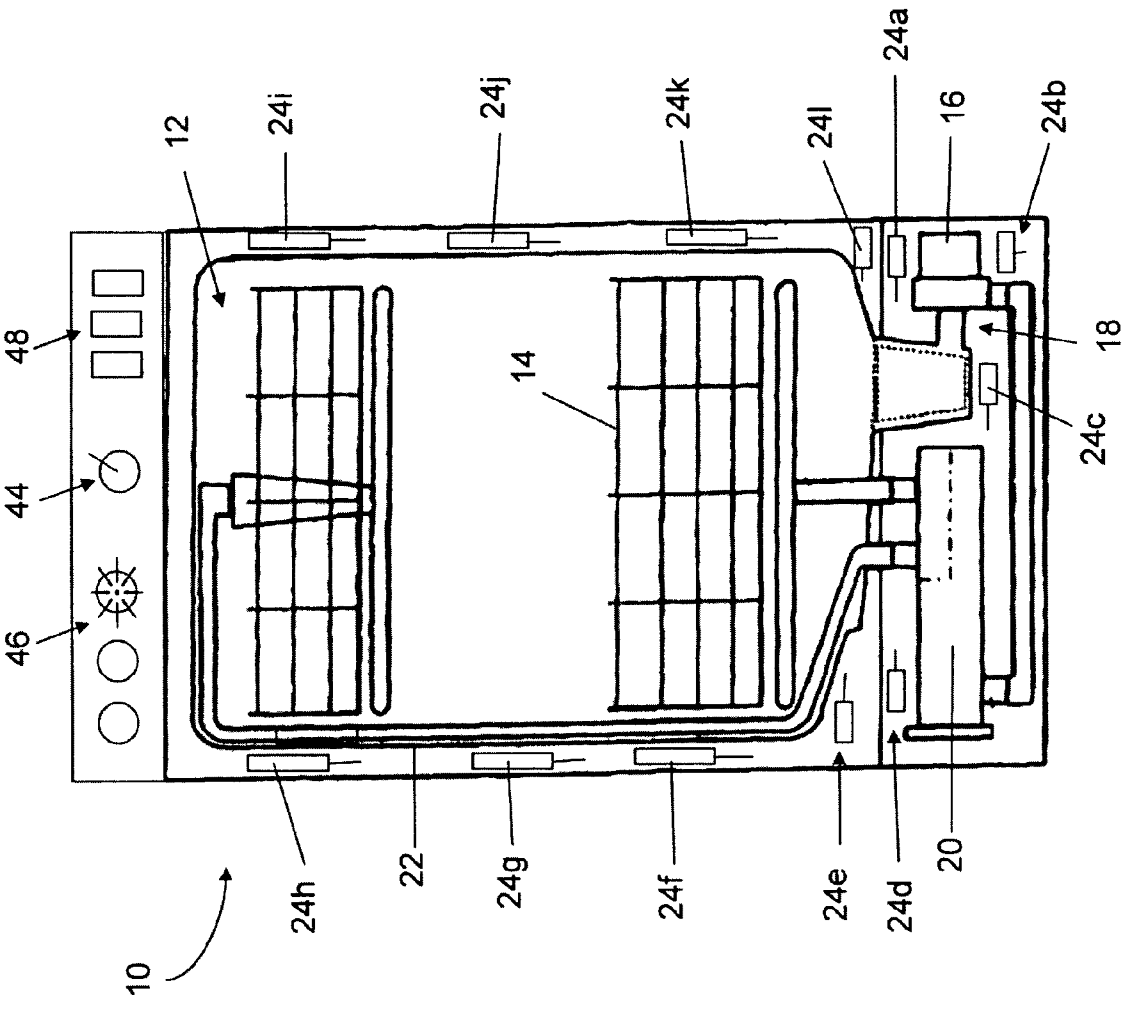
FIG. 3 is a front plan view, in partial section, of a dishwasher configured with another preferred embodiment of the present invention.

With reference now to FIG. 3, the dishwasher 10 is shown configured with another preferred embodiment of the noise reduction apparatus of the present invention has been equipped with an array of piezoelectric sensors 24*a*, 24*b*, 24*c*, 24*d*, 24*e*, 24*f*, 24*g*, 24*h*, 24*i*, 24*j*, 24*k*, and 24*l* disposed strategically in areas of motor noise, flow noise, and other vibrational noise in order to receive and convert a substantial amount of the sound energy waves produced by the device to electric current for feeding to the noise reduction apparatus 26.

The present invention is adaptable for use in a real time monitoring mode or may be coordinated with the respective appliance to operate during different modes of operation of the appliance. For example, and with reference to FIG. 3, the dishwasher 10 may include a wash cycle, a rinse cycle, and a drying cycle. The wash and rinse cycles could, depending on the internal structure of the dishwasher, produce a level of noise discernible to a house occupant in the vicinity of the dishwasher. The drying cycle with no moving water would produce very little, if any, such discernible sound energy. For clarity, the dishwasher 10 is illustrated with a selector switch 44, indicator lights 46, of which one indicator light is illuminated, and basic control switches 48.

Figure 4:
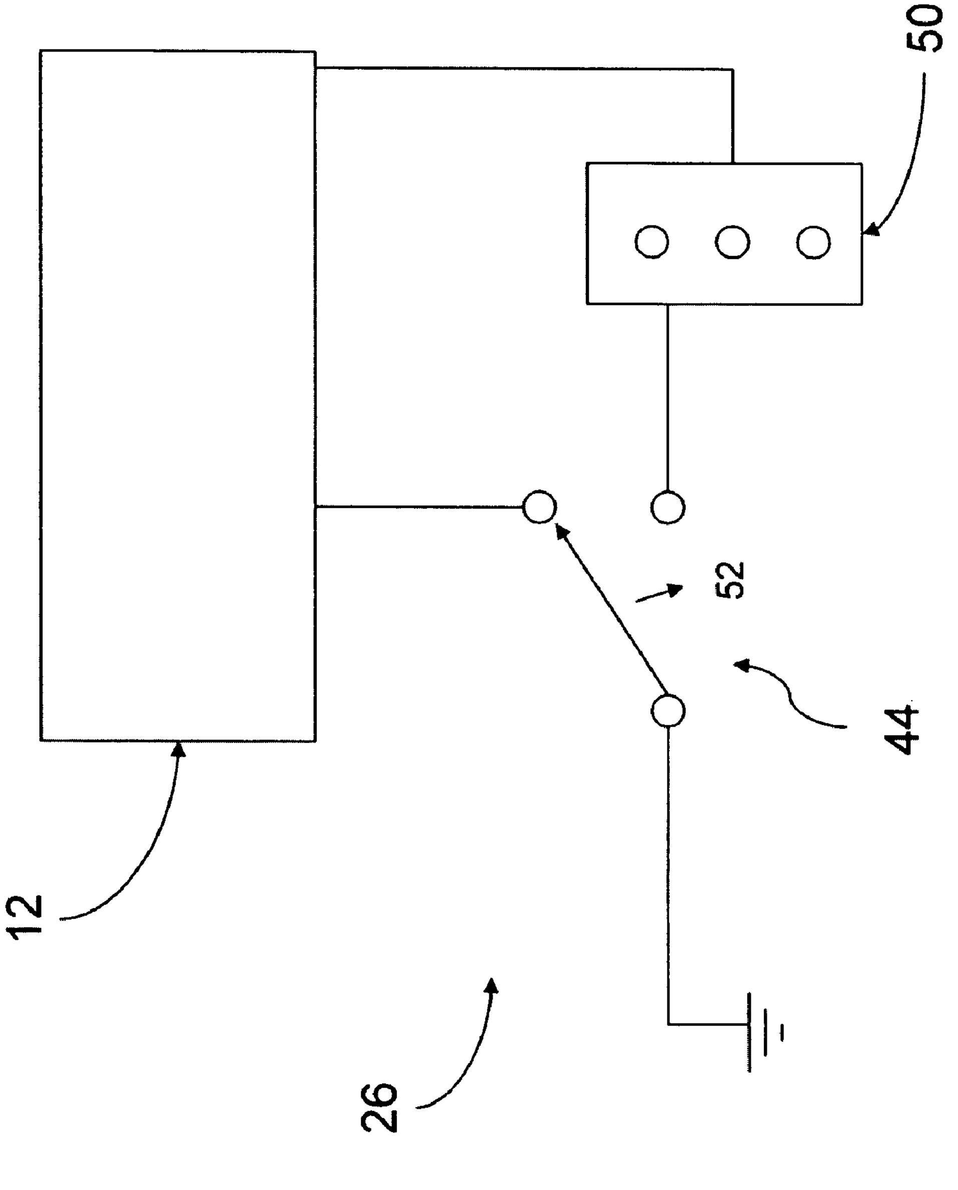
FIG. 4 is a diagrammatic view of an electrical circuit of the present invention according to a further preferred embodiment thereof.

With reference to FIGS. 3 and 4, when the switch 44 is in a first position, as seen in FIG. 4, the real time monitoring mode is engaged and the piezo foil elements and associated circuitry are fully operational at all times. If the switch is moved in the direction shown by the arrow 52 in FIG. 4 to its second position (not shown), its operation becomes dependent upon the mode of operation currently being performed within the washing compartment 12 of the dishwasher 10. Such mode circuitry is illustrated generally at 50. It will be apparent to those skilled in the dishwasher control electronics art that the present invention is easily adaptable to such control circuitry for choosing the operational mode of the noise reduction apparatus 26 of the present invention in light of the operational mode of the dishwasher 10.

In operation and with reference to FIGS. 3 and 4, an operator may select the real time or coordinated mode using the selector switch 44. If the real time mode is chosen, the sensors 24*a*-24*l*, as seen in FIG. 3 are in constant operation so long as the dishwasher is operational as selected by the basic control switches 48. If the coordinated mode is chosen using the selector switch 44, operation of the present apparatus is ongoing in coordination with the dishwasher operational modes.

Whatever the selection, when the present apparatus is active, the sensors 24*a*-24*l* receive sound pressure waves from the noise generating components and are excited thereby to convert the sound pressure wave energy into an electric current, known herein as a sound signal. As is the nature of the passive system described herein, the sound signal may then be shunted directly to ground or even dissipated as heat by the resistors 16.

By the above, the present invention provides a simple and effective passive apparatus for reducing noise emitted by certain household appliances.

It will therefore be readily understood by those persons skilled in the art that the present invention is susceptible of a broad utility and application. While the present invention is described in all currently foreseeable embodiments, there may be other, unforeseeable embodiments and adaptations of the present invention, as well as variations, modifications and equivalent arrangements, that do not depart from the substance or scope of the present invention. The foregoing disclosure is not intended or to be construed to limit the present invention or otherwise to exclude such other embodiments, adaptations, variations, modifications and equivalent arrangements, the present invention being limited only by the claims appended hereto and the equivalents thereof.

I claim:

1. A noise reduction apparatus for altering predetermined sound levels of a sound producing device, the noise reduction apparatus comprising:

at least one piezoelectric sensor disposed relative to the sound producing device such that the at least one piezoelectric sensor is influenced by sound wave energy emitted from the sound producing device with the at least one piezoelectric sensor being operable to convert such sound wave energy into an electric sound signal; and an electric circuit in electrical communication with the at least one piezoelectric sensor for receiving the electric sound signal, the electric circuit including a ground connection and being configured for shunting the electric sound signal to the ground connection, thereby reducing sound heard outside the sound producing device, wherein the at least one piezoelectric sensor includes an array of piezoelectric sensors disposed at spaced intervals relative to the sound producing device, wherein the sound producing device is a selected one of a dishwasher, a clothes washer, a clothes dryer, a refrigerator, a ventilation device, a wine cooler, an espresso making apparatus, a food mixing machine, a food processor, a juice centrifuge, a juice extractor and a waste masticator dishwasher having at least one of a pump and a motor, and a compartment with the array of piezoelectric sensors including at least one sensor disposed within the sound producing device for sensing the at least one of a pump and a motor sound and at least one other sensor disposed adjacent the compartment for sensing sound produced by within the compartment.

2. The noise reduction apparatus according to claim 1 wherein the at least one piezoelectric sensor is one of a foil type sensor and a ceramic type sensor.

3. The noise reduction apparatus according to claim 1 wherein the electric circuit includes at least one resistor for dissipating at least a portion of the electric sound signal as heat.

4. The noise reduction apparatus according to claim 1 wherein the at least one piezoelectric sensor is influenced by sound wave energy emitted from the at least one of a pump and a motor.

5. A noise reduction apparatus for altering predetermined sound levels of a sound producing device, the noise reduction apparatus comprising:

at least one piezoelectric sensor disposed relative to the sound producing device such that the at least one piezoelectric sensor is influenced by sound wave energy emitted from the sound producing device with the at least one piezoelectric sensor being operable to convert such sound wave energy into an electric sound signal; and a first electric circuit in electrical communication with the at least one piezoelectric sensor for receiving the electric sound signal, the electric circuit including a ground connection and being configured for shunting the electric sound signal to the ground connection; and a second electrical circuit in the form of a control circuit in electrical communication with the first electrical circuit for controlling operation thereof, the control circuit having at least two selectively engagable operational modes including a first mode for real-time monitoring of the second electrical signal for controlling a third electrical circuit responsive thereto, and a second mode for operating the third electrical circuit in conjunction with predetermined operational modes of the sound producing device, thereby reducing sound heard outside the sound producing device, wherein the at least one piezoelectric sensor includes an array of piezoelectric sensors disposed at spaced intervals relative to the sound producing device, wherein the sound producing device is a selected one of a dishwasher, a clothes washer, a clothes dryer, a refrigerator, a ventilation device, a wine cooler, an espresso making apparatus, a food mixing machine, a food processor, a juice centrifuge, a juice extractor and a waste masticator dishwasher having at least one of a pump and a motor, and a compartment with the array of piezoelectric sensors including at least one sensor disposed within the sound producing device for sensing the at least one of a pump and a motor sound and at least one other sensor disposed adjacent the compartment for sensing sound produced by within the compartment.

6. The noise reduction apparatus according to claim 5 wherein the at least one piezoelectric sensor is one of a foil type sensor and a ceramic type sensor.

7. The noise reduction apparatus according to claim 5 wherein the electric circuit includes at least one resistor for dissipating at least a portion of the electric sound signal as heat.

* * * * *